United States Patent [19]

Nugent

[11] 4,071,319
[45] Jan. 31, 1978

[54] CONTAMINANT DETECTOR

[75] Inventor: Edward L. Nugent, North Caldwell, N.J.

[73] Assignee: Becton, Dickinson and Company, Rutherford, N.J.

[21] Appl. No.: 745,101

[22] Filed: Nov. 26, 1976

[51] Int. Cl.$^2$ .................. G01N 31/22; G01N 21/06; G01N 1/24
[52] U.S. Cl. ........................ 23/254 R; 23/253 TP; 23/259; 116/114 AM
[58] Field of Search .......... 23/253 TP, 254 R, 253 R, 23/292, 259, 232 R, 255 R; 116/114 AM

[56] References Cited

U.S. PATENT DOCUMENTS

| | | | |
|---|---|---|---|
| 2,487,077 | 11/1949 | Shepherd | 23/253 TP |
| 3,545,930 | 12/1970 | Walker et al. | 23/254 R |
| 3,800,780 | 4/1974 | Elliott | 23/254 R |
| 3,814,079 | 6/1974 | Le Roy | 23/259 X |

*Primary Examiner*—R.E. Serwin
*Attorney, Agent, or Firm*—Kane, Dalsimer, Kane, Sullivan and Kurucz

[57] ABSTRACT

Apparatus for the detection of contaminants in fluids. In the simplest embodiment, the apparatus comprises a vacuum tube having indicator means disposed therein for the detection of a fluid-borne contaminant and a self-sealing, cannula-penetrable closure. The apparatus is operated by piercing the closure with a cannula to draw the fluid for testing into the vacuum chamber.

6 Claims, 4 Drawing Figures

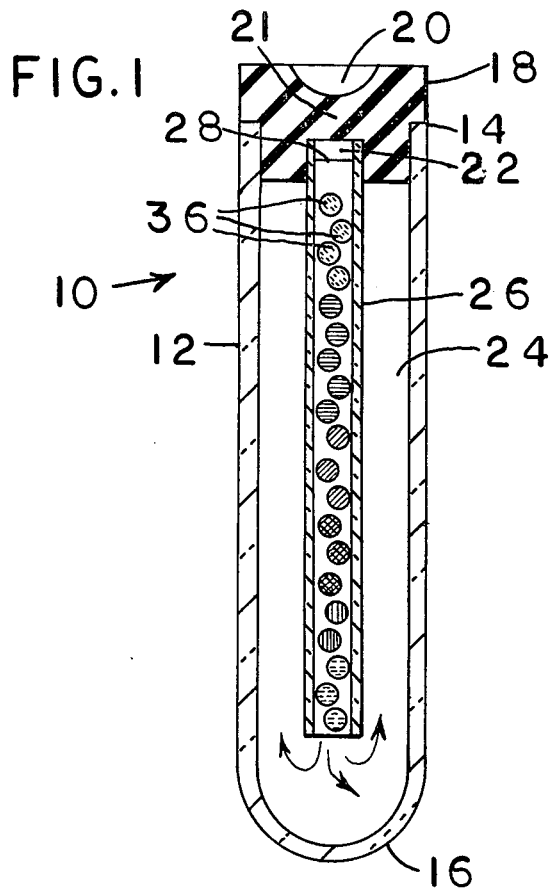

CONTAMINANT DETECTOR

BACKGROUND OF THE INVENTION

1. Field of the Invention

The invention relates to apparatus for detecting fluid-borne contaminants and more particularly relates to portable apparatus which is particularly useful for detecting and/or quantification of contaminants.

2. Brief Description of the Prior Art

It has been stated that instrumentation to detect and measure airborne contaminants is the keystone of an industrial hygiene program; Occupational Hazards, pg. 54 (May, 1974). The reference goes on to stress the importance of small, portable detection devices which could be worn or carried by individual workers subject to the possibility of injury from air-borne contaminants.

Prior hereto, such portable detection devices have been of two general types. The first type comprises a sampling chamber which may contain indicator means and a pump to draw air or other gas to be monitored into the sampling chamber; see for example Occupational Hazards, supra.; Fundamentals of Industrial Hygiene (National Safety Council) pps. 361–366; and U.S. Pat. Nos. 2,489,654; 3,635,092; and 3,768,978. The second type is not generally a direct reading instrument, but comprises a vacuum chamber enclosed by a cannister. The device is merely a collection container and the collected material must be removed for subsequent analysis; see for example U.S. Pat. Nos. 3,618,393 and 3,817,108.

Neither of the previously available types of detector device have been completely satisfactory for all purposes. For example the vacuum chamber device cannot be used to give an instantaneous, direct reading. The pump operated, direct reading instruments on the other hand require skilled manipulation in the field. Very often the accuracy of a testing depends upon the volume of air of gas subjected to testing and/or the rate of air or gas passing in contact with the indicator reagent. These variables are difficult to control without an elaborate and complex pump structure. When the pump is a simple pressure bulb operated by squeezing, it is almost impossible to have reproducible results in samplings.

The apparatus of the invention provides a means of sampling gases and detecting contaminants therein in a highly accurate, reproducible and efficient manner. The volumes and flow rates of the sampled gases are highly controlled. The apparatus of the invention is also useful for detecting contaminants in liquid materials. Examples of contaminants which may be detected with the apparatus of the invention are oxygen, chlorine, methane, ammonia, etc. in air, alcohols, acids, toxins, etc. in liquids and the like.

SUMMARY OF THE INVENTION

The invention comprises apparatus for the detection of fluid-borne contaminants, which comprises:
 a hermetically sealed housing;
 a portal through said housing;
 a self-sealing, gas-proof, cannula penetrable closure for said portal, said closure having an inner face and an outer face;
 means of detecting said contaminants disposed inside said housing; and
 a partial vacuum within said housing.

The term "partial vacuum" as used herein means a gas pressure less than atmospheric pressure, i.e.; less than about 15 lbs. per square inch.

The apparatus of the invention is particularly useful as a portable device for the detection of air-borne contaminants.

BRIEF DESCRIPTION OF THE DRAWINGS

FIG. 1 is a cross-sectional side elevation of an embodiment apparatus of the invention.

FIG. 2 is a cross-sectional side elevation of a preferred embodiment apparatus of the invention.

FIG. 3 is a cross-sectional side elevation of the device of FIG. 2 shown during operation.

FIG. 4 is a cross-sectional side elevation of the device of FIG. 2 shown after operation.

DETAILED DESCRIPTION OF THE PREFERRED EMBODIMENTS

FIG. 1 is a cross-sectional side elevation of an embodiment apparatus 10 of the invention, which comprises a tubular container 12 having an open end 14 and a closed end 16. The open end 14 is hermetically sealed with a self-sealing, cannula-penetrable, gas-proof, elastomeric stopper 18. Stopper 18 may be fabricated from any material having the desired properties, such as for example butyl rubber, natural rubber, RTV-silicone rubber and the like. The tube 12 may be fabricated from any gas-proof material, preferably transparent, such as for example glass. In essence, tube 12 with stopper 18 comprises a hermetically sealed housing for the apparatus of the invention. Entry into the housing through cannula-penetrable stopper 18 is facilitated by a recess 20 in the outer face or surface of stopper 18, thereby creating a thin cannula-penetrable zone 21. A recess 22 on the inner face of stopper 18 is in alignment with zone 21 and receives the cannula inserted through zone 21, Chamber 24 is initially air-evacuated to form a partial vacuum in Chamber 24. Recess 22 also receives in a frictional fit or other suitable means of fit tube 26 which is open at both ends and serves as a support means, bearing packed in its bore 28 analytical reagent material in indicators 36. The indicators may be selected according to the contaminants and media to be tested. Those skilled in the art will know which reagent materials are desirably used for a given use of the apparatus 10; see for example the test indicators described in "Measurement of Air Pollutants", by M. Katz published by World Health Organization Geneva 1969, annex 4, ppgs. 66–99. Preferred as indicators 36 are reagents which change color according to the quantity of a contaminant presence detected. In a preferred embodiment of the invention, tube 26 may be of a precise diameter and have a marking scale or like indicia printed on its body so that one may observe the length of the reagent column which changes color. The degree or quantity of reagent changing color may then be observed and reported according to the printed indicia. Comparative samplings can then be made and comparative reports given. In other words, the determination of the amount of the contaminant would be indicated by the color change (indicating the presence of the contaminant) and the amount of color change in the tube 26 as measured or sighted against a marked scale on the inner tube 26.

The apparatus 10 is operated simply by inserting a cannula through the penetrable zone 21 while maintaining the free end of the cannula in the vicinity of the fluid to be tested so that the vacuum in chamber 24 draws the fluid through the column of indicator 36 in tube 26, the fluid exiting as shown by the arrows in FIG. 1 to chamber 24. Upon filling the vacuum, flow of the fluid past the indicators 36 is terminated and the cannula may be withdrawn to seal chamber 24. The indicators 36 may be observed for an indication of the contaminants presence for which the indicators are expected to respond. As shown in FIG. 1, by the difference in shading, a plurality of different indicators 36 may be used to detect a plurality of contaminants.

Those skilled in the art will appreciate that by the proper selection of chamber 24 capacity and degree of vacuum therein, the volume of fluid to be tested may be precisely controlled by the manufacturer, eliminating the variabilities which might occur if the operator in the field had to take measures to obtain a predetermined volume of fluid for sampling. This of course obviates one of the problems with the personal size detectors of the prior art, which required personal pumping to draw in the sample fluid. Those skilled in the art will also appreciate that the rate of flow of the fluid into chamber 24 may be controlled in the apparatus 10 by pre-determining the degree of porosity of the indicator 36 packed tube 26, i.e.; one can control the porosity of the degree with which the indicators 36 are compacted into the tube 26.

An important advantage of the apparatus 10 is that after use as described above, the sampled fluid is hermetically sealed in chamber 24. Thus, in addition to being tested, the sample is preserved and may be stored for future reference, further analysis, confirmatory analysis etc. Many prior art devices do not have this advantage.

FIG. 2 is a cross-sectional side elevation of a preferred embodiment apparatus of the invention which is in essence a modified apparatus 10, identified as apparatus 10A. Parts of apparatus 10A similar to the parts found in apparatus 10 are similarly numbered in the drawings. The modification in apparatus 10A comprises the addition of lower filter 30 and upper filter 32 in tube 26. These filters can function to remove particulate matter which would block the reagent indicator 36 from functioning. Such filters can also be used to control the rate of flow of a fluid such as air, by their porosity. Further, the filter 30 can also function simply as a means of retaining indicator 36 in the tube 26.

The apparatus 10A also differs from apparatus 10 in that there is a piston 34 component mounted on the shaft of tube 26 by frictional engagement between bore 40 in piston 34 and the tube 26. In the most preferred embodiment, bore 40 is lined with surface bearing 42 to maintain a sliding-seal between piston 34 and tube 26. The piston 34 has a top surface 38 and a lower surface 39 and divides chamber 24 so as to create a sub-chamber 46. The outer periphery of piston 34 includes sealing ribs 44 which form a sliding seal with the inside walls of tube 12. The piston 34 may function to control the rate of flow of fluid, such as a gas into the apparatus 10A. The control is obtained by constructing the piston dimensions so as to be movable only under certain pressure differentials between surfaces 38 and 39 or only at a certain speed. This is done by the control of the degree of fit and/or choice of material of the piston 34 in the apparatus 10A. The piston may also function as a means of measuring the volume of fluid sample being taken into the apparatus 10A as will be appreciated referring to FIG. 3.

FIG. 3 is a view of apparatus 10A as shown in FIG. 2 but after penetration of zone 21 with a cannula, permitting the entry of air through tube 26 and into lower chamber 46. The lower pressure on surface 38 of the piston 34 results in movement of the piston 34 upward, expanding chamber 46 and contracting chamber 24. If indicia are applied to tube 12, one can measure the movement of piston 34 and determine the volume of air sample taken in. One could then terminate air intake at any desired point, or as shown in FIG. 4 permit the entire apparatus 10A to be filled with air sample.

FIG. 4 shows the apparatus 10A after the piston 34 has traveled its maximum distance. At this point the cannula may be withdrawn to seal the apparatus 10A. As also shown in FIG. 4, when compared with FIG. 3, the reagent indicators 36 have changed in appearance above particles 50, indicating the presence (and amount if tube 26 contained indicia) of some contaminant in the air sample taken into apparatus 10A.

Those skilled in the art will appreciate that many modifications may be made to the device of the invention as described above without departing from the spirit and the scope of the invention. For example, for cases where only a sample is to be drawn and then taken to the laboratory for further analysis, the inner tube 26 need not contain any reagent 36. The piston 34 would initially be mated flush with the bottom of the outer tube 12 which preferably would be flat. This feature will provide a device for collection only and would eliminate any contamination of the sample from residuals due to manufacturing (an absolute vacuum or total air removal is not ideally possible).

I claim:
1. Apparatus for the detection of fluid-borne contaminants, which comprises:
   a. a first tubular container having a portal therein;
   b. a self-sealing, gas-proof, cannula-penetrable closure mounted in said portal, said closure together with said first tubular container defining a hermetically sealed chamber;
   c. a partial vacuum in said chamber;
   d. a second tubular container mounted in said first tubular container and having one end in open communication with said chamber and the other end closed by said closure; and
   e. an indicator for the presence of said contaminants disposed in said second tubular container.

2. Apparatus according to claim 1 wherein said indicators are enclosed within said second tubular container by a fluid permeable filter.

3. The apparatus of claim 1 which includes means for dividing said chamber into upper and lower compartments sealed from each other, the open end of said second tubular container being in communication with said lower compartment and said means being movable to change the relative size of said compartments.

4. The apparatus of claim 3 wherein said means for dividing comprises a piston, slidingly mounted on said second tube and forming a sliding seal with the inner walls of said first container and the outer walls of said second container.

5. The apparatus of claim 4 wherein said piston includes a frictional bearing surface for engagement with the outer walls of said second container.

6. The apparatus of claim 1 wherein said indicator will detect the presence of a plurality of contaminants.

* * * * *